United States Patent
Quist

(10) Patent No.: US 8,019,135 B2
(45) Date of Patent: Sep. 13, 2011

(54) APPARATUS AND METHOD FOR PROVIDING 2D REPRESENTATION OF 3D IMAGE DATA REPRESENTING AN ANATOMICAL LUMEN TREE STRUCTURE

(75) Inventor: Marcel Johannes Quist, Eindhoven (NL)

(73) Assignee: Koninklijke Philips Electronics N. V., Eindhoven (NL)

( * ) Notice: Subject to any disclaimer, the term of this patent is extended or adjusted under 35 U.S.C. 154(b) by 1038 days.

(21) Appl. No.: 11/817,693

(22) PCT Filed: Mar. 6, 2006

(86) PCT No.: PCT/IB2006/050690
§ 371 (c)(1),
(2), (4) Date: Sep. 4, 2007

(87) PCT Pub. No.: WO2006/095302
PCT Pub. Date: Sep. 14, 2006

(65) Prior Publication Data
US 2008/0205728 A1    Aug. 28, 2008

(30) Foreign Application Priority Data
Mar. 9, 2005   (EP) ..................................... 05101805

(51) Int. Cl.
*G06K 9/00*    (2006.01)
(52) U.S. Cl. .............................. 382/128; 128/922; 378/4
(58) Field of Classification Search .................... 382/10, 382/128–132; 128/922; 378/4–27
See application file for complete search history.

(56) References Cited

U.S. PATENT DOCUMENTS

| | | | |
|---|---|---|---|
| 6,385,332 B1 * | 5/2002 | Zahalka et al. | 382/128 |
| 6,728,566 B1 | 4/2004 | Subramanyan | |
| 6,782,284 B1 | 8/2004 | Subramanyan | |
| 7,203,353 B2 * | 4/2007 | Klotz et al. | 382/131 |
| 7,369,691 B2 * | 5/2008 | Kondo et al. | 382/128 |
| 2002/0106116 A1 | 8/2002 | Knoplioch | |
| 2002/0114503 A1 | 8/2002 | Klotz | |
| 2003/0078500 A1 | 4/2003 | Evron | |
| 2003/0103665 A1 * | 6/2003 | Uppaluri et al. | 382/131 |
| 2004/0066958 A1 | 4/2004 | Chen | |
| 2007/0019846 A1 * | 1/2007 | Bullitt et al. | 382/128 |
| 2008/0101675 A1 * | 5/2008 | Guiliguian et al. | 382/131 |
| 2009/0060298 A1 * | 3/2009 | Weijers et al. | 382/128 |

OTHER PUBLICATIONS

Kanitsar A. et al "CPR—Curved Planar Reformation" Institute of Electrical and Electronics Engineers IEEE Visualization 2002. Boston, MA Oct. 27-Nov. 1, pp. 37-44.

* cited by examiner

*Primary Examiner* — Anand Bhatnagar

(57) ABSTRACT

A CT imaging apparatus (2) for providing a 2D representation of 3D image data representing a pulmonary vessel tree of a patient is disclosed. The apparatus comprises X-ray sources (6) and detectors (8) arranged in pairs for generating 3D image data representing a plurality of positions along lumen branches of the vessel tree and for receiving 3D image data representing at least one anatomical property at each of the locations. A processor (20) processes the 3D image data to provide 2D image data displayed on a display device (24) such that each lumen branch is represented by a line, and the color of each portion of a line representing one of the positions varies in dependence upon the anatomical property being measured.

13 Claims, 3 Drawing Sheets

Distance to periphery (mm)

APPARATUS AND METHOD FOR PROVIDING 2D REPRESENTATION OF 3D IMAGE DATA REPRESENTING AN ANATOMICAL LUMEN TREE STRUCTURE

The present invention relates to an apparatus and method for providing a two-dimensional (2D) representation of three-dimensional (3D) image data representing an anatomical lumen tree structure. The invention relates particularly, but not exclusively, to an apparatus and method for providing a compressed 2D visualization of pulmonary blood vessel characteristics. The invention also relates to a computer program product for use in such apparatus.

Pulmonary embolism is a life-threatening condition involving blood clotting in the lungs. It is known to detect pulmonary emboli by means of high resolution, contrast enhanced thorax computer tomograph (CT) scans. A CT scanner generates image data of transverse slices through a patient's thorax, and a 3D model of the patient's pulmonary blood vessel tree is formed by the CT scanner. The 3D image data is then displayed on a monitor, and the image of the pulmonary vessel tree is inspected by a radiographer performing visual assessment of individual image slices, and manually scrolling through the image stack.

This known process suffers from the drawback that the pulmonary vessel tree structure is geometrically very complex, and extends typically over 100-400 CT slices, which makes inspection very difficult and time consuming. The process therefore requires highly specialized skills and shows high user variability, as a result of which it is difficult to automate the process.

In addition, the existing presentation of computer aided detection results suffers from the drawback that only positive findings can be reported as being present, and the user cannot be sure whether negative findings result from a healthy situation or from failure of the detection process.

It is an object of the present invention to provide an improved apparatus and process for providing a 2D representation of 3D image data representing an anatomical lumen tree structure.

According to an aspect of the present invention, there is provided an apparatus for providing a 2D representation of 3D image data representing an anatomical lumen tree structure, the apparatus comprising:

at least one first input for receiving first data representing a respective first distance of a plurality of positions along at least one lumen branch from a respective starting point on said lumen branch;

at least one second input for receiving second data representing at least one anatomical property of the corresponding said lumen branch at each of said locations;

at least one processor, connected to at least one said first input and at least one said second input, for processing said first and second data to provide third data adapted to be displayed on at least one display device such that at least one said lumen branch is represented by a respective line, at least one said first distance is represented by a respective second distance along the corresponding said line, and the appearance of a respective portion of said line representing the or each said position varies in dependence upon said anatomical property.

This provides the advantage of enabling several branches of the lumen tree to be displayed simultaneously, as a result of which a radiologist can more quickly determine the relationship between neighboring slices of CT image data. The present invention also provides the advantage of enabling analysis of the displayed 2D data to be automated, for example by means of suitable algorithms.

At least one said processor may be adapted to provide said third data indicating the absence of said anatomical property at at least one said position.

This provides the advantage of enabling easier detection of anatomical abnormalities or failure of the imaging process used.

At least one said processor may be adapted to provide said third data enabling a plurality of said lines to be displayed simultaneously on at least one said display device.

At least one said processor may be adapted to provide a link between said third data and said first and/or second data to enable a respective 3D image corresponding to at least one said portion of a said line to be displayed on at least one display device.

This provides the advantage of enabling a radiologist to rapidly match an area of interest of the display with the corresponding 3D image, for example an image slice provided by a CT scanner.

At least one said processor may be adapted to determine a respective derivative of at least one said anatomical property with respect to distance along the corresponding said lumen branch at at least one said location.

This provides the advantage of rapidly determining isolated regions where the anatomical property is different from that at adjacent regions on both sides along the corresponding lumen branch, which may indicate abnormalities. This also provides the advantage of enabling the detection of such regions to be automated.

According to another aspect of the present invention, there is provided an apparatus for displaying a 2D representation of 3D image data representing an anatomical lumen tree structure, the apparatus comprising an apparatus as defined above and at least one display device.

The apparatus may further comprise at least one imaging apparatus for providing said first and second data.

According to a further aspect of the present invention, there is provided a method for providing a 2D representation of 3D image data representing an anatomical lumen tree structure, the method comprising:

receiving first data representing a respective first distance of a plurality of positions along at least one lumen branch from a respective starting point on said lumen branch;

receiving second data representing at least one anatomical property of the corresponding said lumen branch at each of said positions; and processing said first and second data to provide third data adapted to be displayed on at least one display device such that at least one said lumen branch is represented by a respective line, at least one said first distance is represented by a respective second distance along the corresponding said line, and the appearance of a respective portion of said line representing the or each said position varies in dependence upon said anatomical property.

The third data may be adapted to indicate the absence of said anatomical property at at least one said position.

The third data may be adapted to be displayed such that a plurality of said lines are displayed simultaneously.

The color of said portions of said lines may vary in dependence upon said anatomical property.

Said anatomical property may be the width of a lumen available for fluid flow, and/or the width of a region of flowing fluid in the lumen, and/or the rate of fluid flow in the lumen.

The method may further comprise the step of providing a link between said third data and said first and/or second data to enable a respective 3D image corresponding to at least one said portion of a said line to be displayed on at least one display device.

The method may further comprise the step of determining a respective derivative of at least one said anatomical property with respect to distance along the corresponding said lumen branch at at least one said location.

According to a further aspect of the present invention, there is provided a method of displaying a 2D representation of 3D image data representing an anatomical lumen tree structure, the method comprising:

providing third data by means of a method as defined above; and displaying said third data on at least one display device.

The method may further comprise the step of providing said first and second data.

According to a further aspect of the present invention, there is provided a data structure for use by a computer system for providing a 2D representation of 3D image data representing an anatomical lumen tree structure, the data structure including:

first computer code executable to receive first data representing a respective first distance of a plurality of positions along at least one lumen branch from a respective starting point on said lumen branch;

second computer code executable to receive second data representing at least one anatomical property of the corresponding said lumen branch at each of said positions; and third computer code executable to process said first and second data and provide third data adapted to be displayed on at least one display device such that at least one said lumen branch is represented by a respective line, at least one said first distance is represented by a respective second distance along the corresponding said line, and the appearance of a respective portion of said line representing the or each said position varies in dependence upon said anatomical property.

The data structure may further include fourth computer code executable to indicate the absence of said anatomical property at at least one said location.

The data structure may further include fifth computer code executable to display a plurality of said lines simultaneously on at least one said display device.

The data structure may further include sixth computer code executable to provide a link between said third data and said first and/or second data to enable a respective 3D image corresponding to at least one said portion of a said line to be displayed on at least one said display device.

The data structure may further include seventh computer code executable to determine a respective derivative of at least one said anatomical property with respect to distance along the corresponding said lumen branch at at least one said location.

According to a further aspect of the present invention, there is provided a computer readable medium carrying a data structure as defined above stored thereon.

A preferred embodiment of the invention will now be described, by way of example only and not in any limitative sense, with reference to the accompanying drawings, in which.

Figure 1:
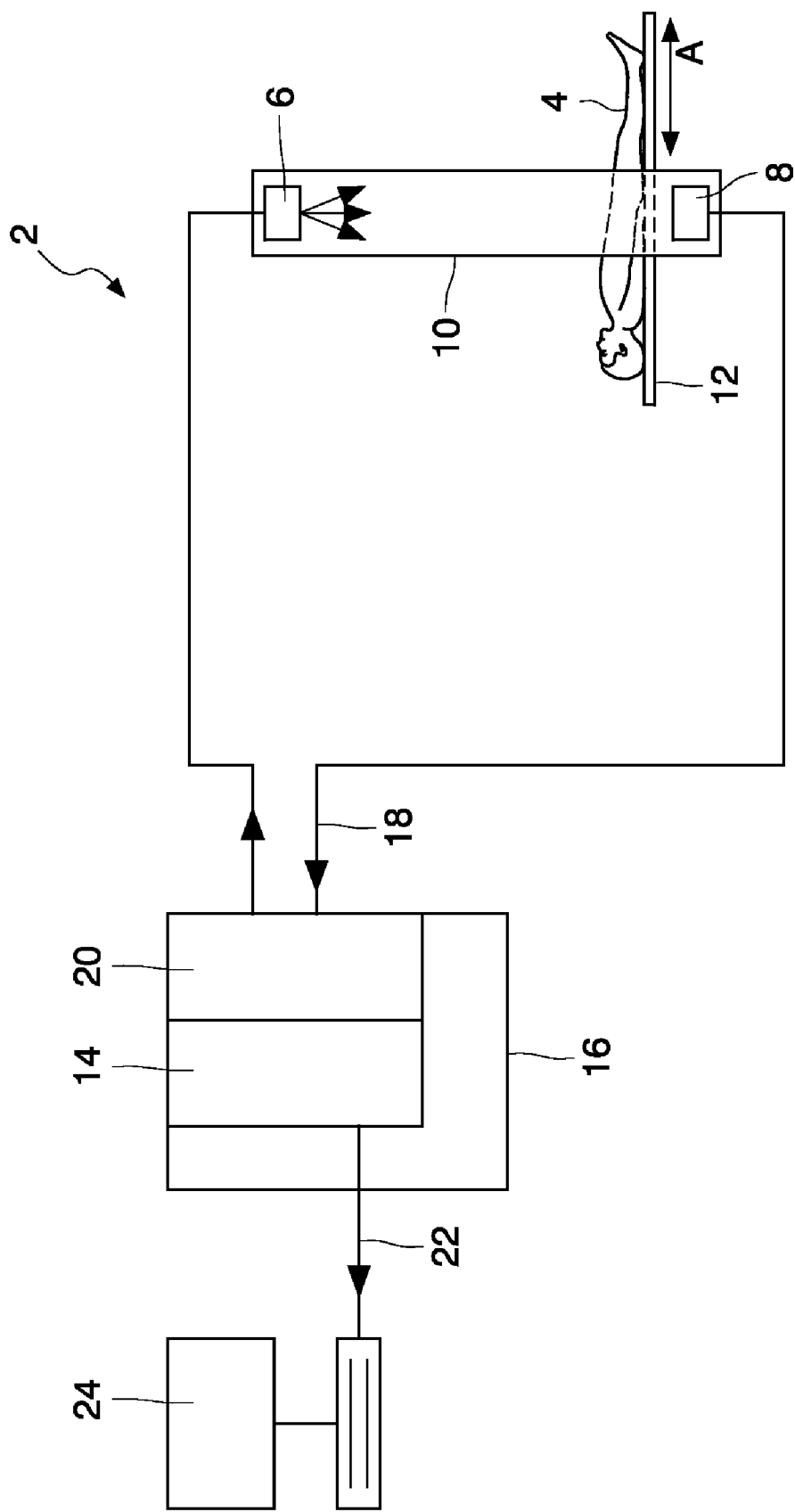
FIG. 1 is a schematic representation of a high resolution, contrast enhanced thorax computer tomography (CT) scanning apparatus embodying the present invention.

Referring to FIG. 1, a computer tomography (CT) scanner apparatus 2 for forming a 3D imaging model of a thorax of a patient 4 has an array of X-ray sources 6 and detectors 8 arranged in source/detector pairs in a generally circular arrangement around a support 10. The apparatus is shown from the side in FIG. 1, as a result of which only one source/detector pair can be seen.

The patient 4 is supported on a platform 12 which can be moved by suitable means (not shown) in the direction of arrow A in FIG. 1 under the control of a control unit 14 forming part of a computer 16. The control unit 14 also controls operation of the X-ray sources 6 and detectors 8 for obtaining image data of a thin section of the patient's body surrounded by support 10, and movement of the patient 4 relative to the support 10 is synchronized by the control unit 14 to build up a series of images of the patient's thorax, typically a stack of 100 to 400 images.

The image data obtained from the detectors 8 is input via input line 18 to a processor 20 in the computer 16, and the processor 20 builds up a 3D model of the patient's pulmonary vessel tree from the data image slices. The processor 20 also outputs 3D image data along output line 22 to a suitable monitor 24 to display a 3D image of the pulmonary vessel tree.

Figure 3:
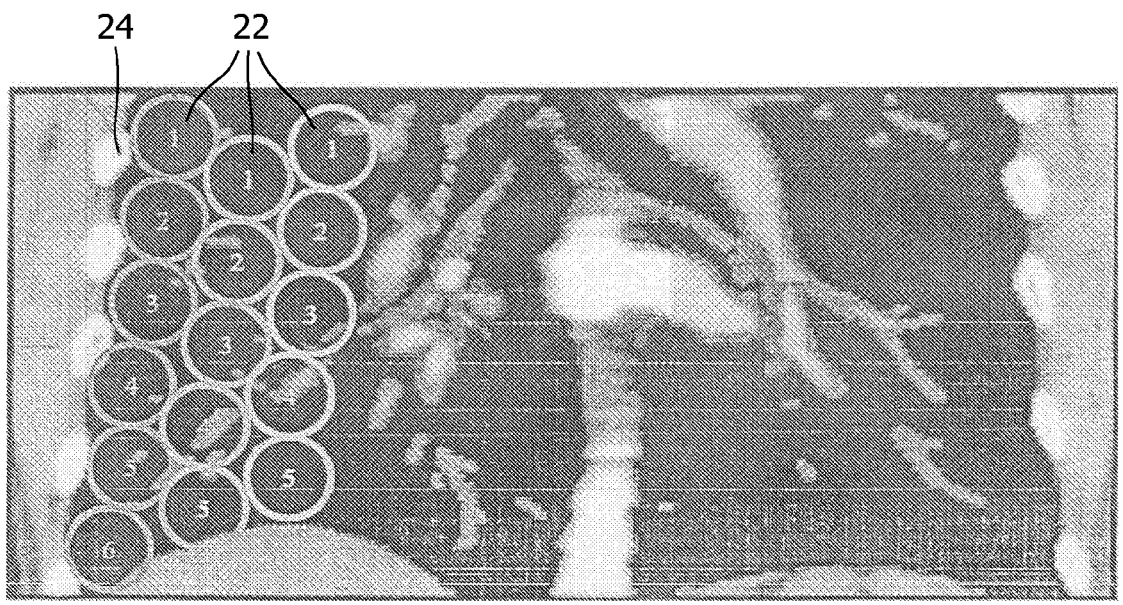
FIG. 3 is a detailed view of a 3D image of the pulmonary vessel tree showing regions of interest for carrying out a method embodying the present invention.
Figure 4:
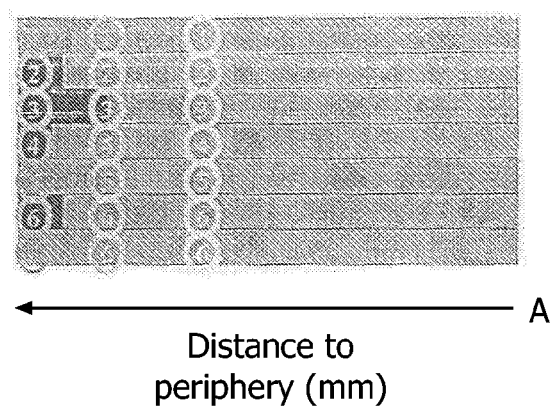
FIG. 4 is a schematic representation of a 2D representation of the pulmonary vessel tree of FIG. 3.

Referring now to FIGS. 3 and 4, the processor 20 first segments the image data of the patient's lungs, i.e. identifies the data relating to the lungs. The processor 20 then divides the image data from the patient's lungs into two left and three right lobes, in order to present the 2D representation of the data in as comprehensive and anatomically convenient a manner as possible. The processor 20 then segments the pulmonary vessel tree, i.e. determines the image data relating to the pulmonary vessel tree by first identifying the main branches originating in each of the five lobes of the lungs. This can be achieved in a number of manners familiar to persons skilled in the art.

Subsequently to segmentation of the data relating to the pulmonary vessel tree, a starting point (not shown) in the pulmonary artery is indicated, and a wave front propagation technique familiar to persons skilled in the art is applied along each branch of the pulmonary vessel tree as far as the branch end points. The end points of the vessel tree are then determined, and region of interest layers 22 starting at the periphery 24 of the lungs are defined, and in each region of interest 22, an end point is detected and a path is tracked towards the starting point on the pulmonary artery. At selected points along the path, measurements of one or more physiological parameters such as vessel diameter, lumen intensity, or local contrast.

The processor 20 may also determine the second derivative of one or more of these anatomical parameters with respect to distance along the corresponding lumen branch. This gives an indication of, for example, a dark region (representing low blood flow or lack of blood flow) bounded on both sides by lighter regions, which may indicate an abnormality such as a pulmonary embolism, and enables the detection of such abnormalities to be automated and therefore carried out more rapidly.

The processor 20 then maps the measurement of the or each physiological parameter to each point for a pulmogram display 26 (FIG. 2) for each lobe. The number of detected points along each branch in a given lobe indicates the length of the branch, and the color of a particular part of the branch is varied according to the value of the physiological parameter measured at that location. Each branch of the vessel tree is represented in the pulmogram display 26 by a line 28. In this way, all of the detected tree branches of a particular lobe are presented in a single view to the radiologist, and all path measurements of the detected branches, healthy as well as abnormal, are displayed. The display enables the expert such as a radiologist to assess the vessel tree characterization directly from a 2D display that covers the entire vessel tree.

Figure 2:
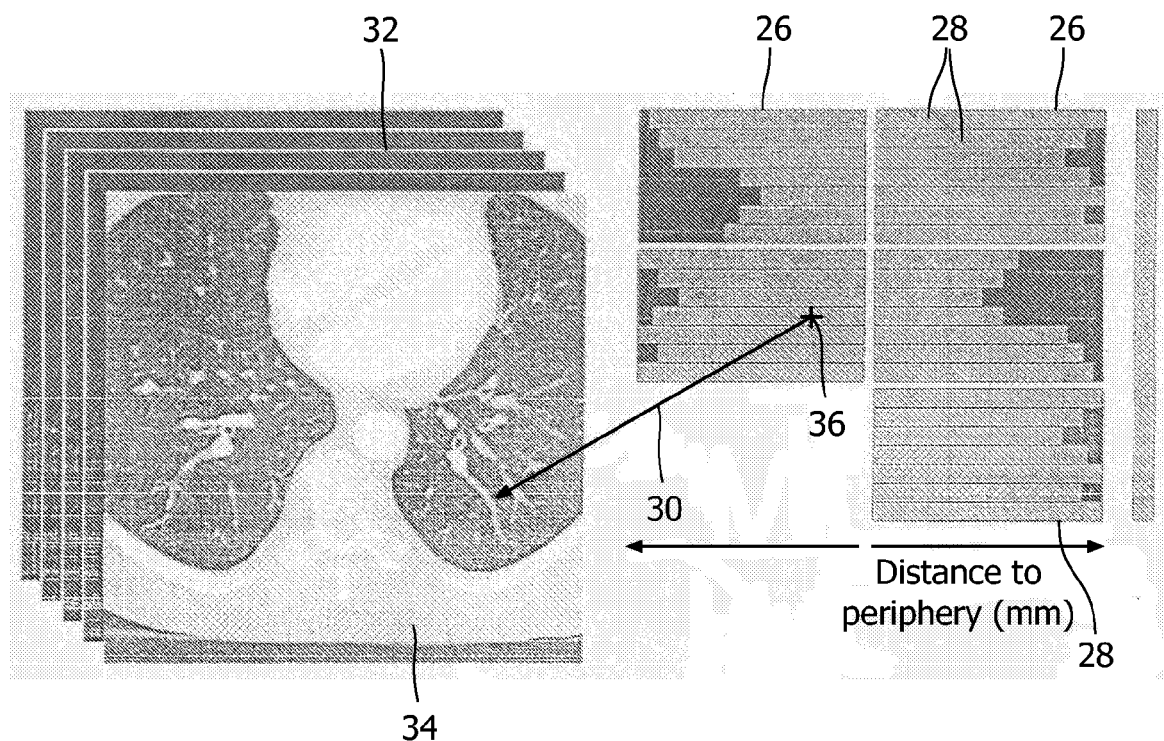
FIG. 2 is a schematic representation of a 3D image stack of a pulmonary vessel tree formed by means of the apparatus of FIG. 1, together with a corresponding schematic 2D representation provided by the apparatus of FIG. 1.

As shown in FIG. 2, the processor 20 also provides a link 30 from the pulmogram display 26 to the original image data stack 32, as a result of which the expert can selectively inspect the 3D image slice 34 corresponding to an area of interest 36 in the pulmogram.

The 2D pulmogram display shown in FIGS. 2 and 4 has a number of significant advantages. Firstly, it indicates when large parts of the vessel tree have not been detected. This suggests either a pathological abnormality, or a failure of the detection algorithm. The former may give rise to closer inspection, and the latter warns of potential false negatives generated by the algorithm.

The pulmogram also has the advantage that a blockage in one of the paths can be quickly determined. This may be as a result, for example, of a pulmonary embolism, in which case the embolism can be quickly detected by a radiologist from inspection of the pulmogram shown in FIG. 2. In addition, a suitable algorithm can be executed by the processor 20 to automatically detect potential abnormalities.

It will be appreciated by persons skilled in the art that the above embodiment has been described by way of example only, and not in any limitative sense, and that various alterations and modifications are possible without departure from the scope of the invention as defined by the appended claims. For example, although the above described embodiment relates to the pulmonary vessel tree, the present invention can also be used to present a 2D representation of any other lumen vessel tree, such as the bronchial tree or vascular tree, for instance an arterial tree. Also, the 2D representation need not consist of straight lines as shown in FIGS. 2 and 4, but could be non-straight lines where the distance of a location along a branch of the lumen tree is represented on a display by a distance along the line from a predetermined starting point.

The invention claimed is:

1. An apparatus (2) for providing a 2D representation (26) of 3D image data representing an anatomical lumen tree structure comprising a plurality of lumen branches, the apparatus comprising:—
    at least one first input (18) for receiving first data representing a respective first distance of a plurality of positions along each lumen branch from a respective starting point on said each lumen branch;
    at least one second input (18) for receiving second data representing at least one anatomical property of the corresponding said each lumen branch at each of said positions;
    at least one processor (20), connected to at least one said first input and at least one said second input, for processing said first and second data to provide third data adapted to be displayed on at least one display device such that said each lumen branch is represented by a respective line (28), at least one said first distance is represented by a respective second distance along the corresponding said line, and the appearance of a respective portion of said line representing each of said positions varies in dependence upon said anatomical property.

2. An apparatus according to claim 1, wherein at least one said processor is adapted to provide said third data indicating the absence of said anatomical property at least one said position.

3. An apparatus according to claim 1, wherein at least one said processor is adapted to provide said third data enabling a plurality of said lines to be displayed simultaneously on at least one said display device.

4. An apparatus according to claim 1, wherein at least one said processor is adapted to provide a link (30) between said third data and said first and/or second data to enable a respective 3D image corresponding to at least one said portion of a said line to be displayed on at least one display device.

5. An apparatus according to claim 1, wherein at least one said processor is adapted to determine a respective derivative of at least one said anatomical property with respect to distance along the corresponding said lumen branch at least one said location.

6. An apparatus for displaying a 2D representation of 3D image data representing a anatomical lumen tree structure, the apparatus comprising an apparatus according to claim 1 and at least one display device (24).

7. An apparatus according to claim 6, further comprising at least one imaging apparatus (6,8) for providing said first and second data.

8. A method performed by an imaging apparatus for providing a 2D representation of 3D image data representing an anatomical lumen tree structure comprising a plurality of lumen branches, the method comprising:
    receiving first data representing a respective first distance of a plurality of positions along each lumen branch from a respective starting point on said each lumen branch;
    receiving second data representing at least one anatomical property of the corresponding said each lumen branch at each of said positions; and
    processing said first and second data to provide third data adapted to be displayed on at least one display device such that said each lumen branch is represented by a respective line, at least one said first distance is represented by a respective second distance along the corresponding said line, and the appearance of a respective portion of said line representing each of said positions varies in dependence upon said anatomical property.

9. A method according to claim 8, wherein the colour of said portions of said lines varies in dependence upon said anatomical property.

10. A method according to claim 8, wherein said anatomical property is the width of a lumen available for fluid flow, and/or the width of a region of flowing fluid in the lumen, and/or the rate of fluid flow in the lumen.

11. A method of displaying a 2D representation of 3D image data representing an anatomical lumen tree structure, the method comprising:—
    providing third data by means of a method according to claim 8; and
    displaying said third data on at least one display device.

12. A method according to claim 11, further comprising the step of providing said first and second data.

13. A computer readable storage medium for storing a data structure for use by a computer system for providing a 2D representation of 3D image data representing an anatomical lumen tree structure comprising a plurality of lumen branches, the data structure including:—
    first computer code executable to receive first data representing a respective first distance of a plurality of positions along each lumen branch from a respective starting point on said each lumen branch;

second computer code executable to receive second data representing at least one anatomical property of the corresponding said each lumen branch at each of said positions; and third computer code executable to process said first and second data and provide third data adapted to be displayed on at least one display device such that said each lumen branch is represented by a respective line, at least one said first distance is represented by a respective second distance along the corresponding said line, and the appearance of a respective portion of said line representing each of said position varies in dependence upon said anatomical property.

* * * * *